United States Patent
Abramov et al.

[11] Patent Number: 5,806,512
[45] Date of Patent: Sep. 15, 1998

[54] CARDIAC/PULMONARY RESUSCITATION METHOD AND APPARATUS

[75] Inventors: Vladimir Victorovich Abramov, Moscow, Russian Federation; Robert M. Hamilton, Brea, Calif.; Michael G. Flood, Pensacola, Fla.

[73] Assignee: Life Support Technologies, Inc., Pensacola, Fla.

[21] Appl. No.: 736,444

[22] Filed: Oct. 24, 1996

[51] Int. Cl.$^6$ ............................ A61H 31/00; A61H 16/00
[52] U.S. Cl. ................................ 128/204.18; 128/204.21; 601/41; 601/150
[58] Field of Search .................... 128/200.24, 204.18, 128/202.12, 205.26; 601/41, 42, 43, 44, 149, 150, 151, 152

[56] References Cited

U.S. PATENT DOCUMENTS

| | | | |
|---|---|---|---|
| 3,880,149 | 4/1975 | Kawaguchi | 601/150 |
| 4,349,015 | 9/1982 | Alferness | 601/41 |
| 4,397,306 | 8/1983 | Weisfeldt et al. | 601/41 |
| 4,424,806 | 1/1984 | Newman et al. | 601/41 |
| 4,753,226 | 6/1988 | Zheng et al. | 601/150 |
| 4,770,165 | 9/1988 | Hayek | 128/202.12 |
| 4,930,498 | 6/1990 | Hayek | 128/205.26 |
| 5,036,841 | 8/1991 | Hamilton | 128/202.26 |
| 5,327,887 | 7/1994 | Nowakowski | 128/204.21 |
| 5,370,603 | 12/1994 | Newman | 601/41 |
| 5,490,820 | 2/1996 | Schock et al. | 601/41 |
| 5,514,079 | 5/1996 | Dillon | 601/151 |

FOREIGN PATENT DOCUMENTS

92/00716  1/1992  WIPO ...................................... 601/41

OTHER PUBLICATIONS

Compression Techniques & Blood Flow during Cardiopulmonary Resuscitation, *Respiratory Care*, Apr. 1995, pp. 380–392.

*Primary Examiner*—Mickey Yu
*Assistant Examiner*—Virendra Srivastava
*Attorney, Agent, or Firm*—Harold L. Jackson

[57] ABSTRACT

A method and apparatus for resuscitating the cardiac/pulmonary activity of a patient includes the use of pneumatically controlled inflatable/deflatable cuffs secured over the patient's legs and abdomen and optionally the chest. The cuffs are preferably inflated and deflated at a cyclical rate of 10–40 cycles/min. with the inflation/deflation mode of the chest cuff, if used, being out-of-phase with the operation of the abdominal cuff. A ventilator and face mask may be used to supply breathable air to the patient's airway in conjunction with the cyclical operation of the cuffs.

24 Claims, 3 Drawing Sheets

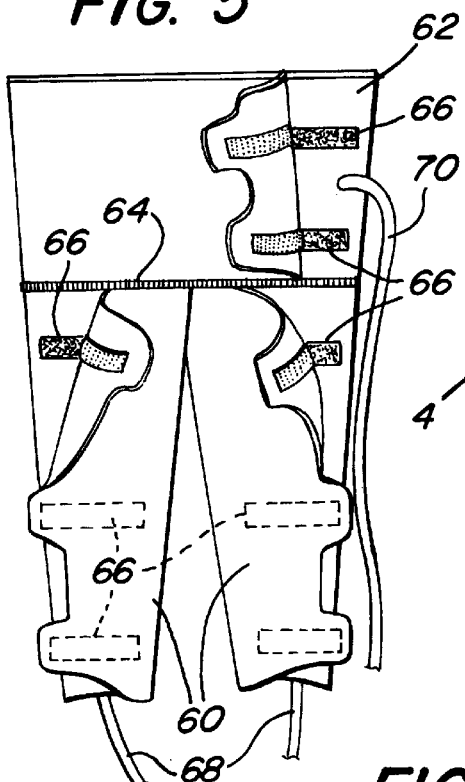
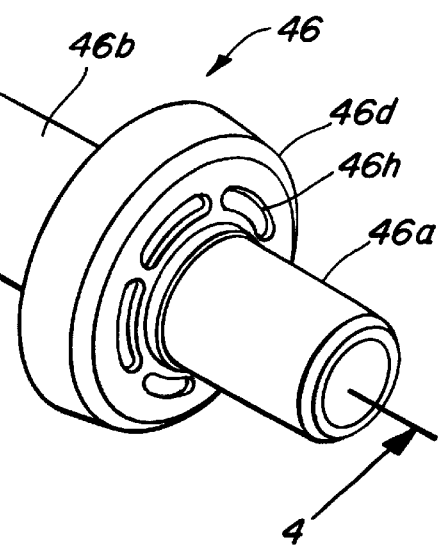
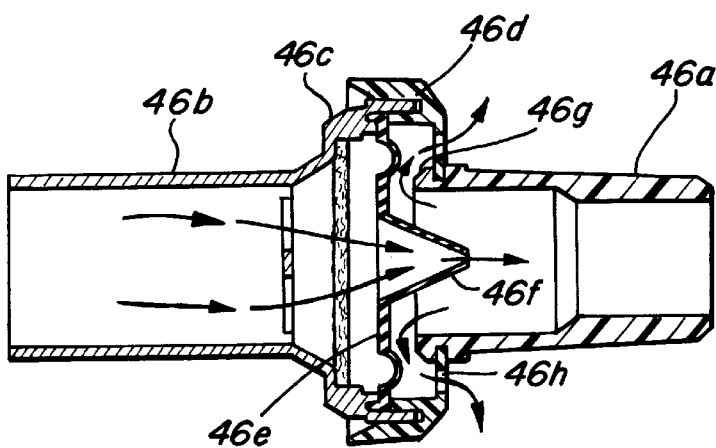

CARDIAC/PULMONARY RESUSCITATION METHOD AND APPARATUS

FIELD OF THE INVENTION

This invention relates to a method and apparatus for providing cardiac and/or pulmonary resuscitation.

DESCRIPTION OF THE PRIOR ART

The conventional method of providing external cardiac resuscitation, i.e., external cardiac massage, involves the application of mechanical pressure on the patient's chest, for example, by means of a person's hands or a mechanical manipulator. However, the effectiveness of such method is very much dependent upon the technique used and it tends to interfere with pulmonary resuscitation since it involves manipulation of the chest. The technique is difficult to automate and is tiring where the hands are used for extended periods. Furthermore, the rate of blood circulation achieved by this method is low and the method carries a relatively high risk of bone and tissue damage.

Less conventional heart resuscitation methods have been reported in the U.S. Medical literature which involved the use of inflatable CPR vests. The vests are designed to be placed around a patient's chest and inflated and deflated in a manner similar to manual CPR methods. See an article entitled "Compression Techniques and Blood Flow during Cardiopulmonary Resuscitation" in the April 1995 issue of Respiratory Case, pages 380–392.

A method of using pneumatic sleeves (or cuffs) placed around a patient's legs and abdomen to increase the flow of blood through the arteries supplying blood to the heart muscles to provide therapeutic treatment for angina was discussed on NBC's Evening News program (U.S. Television) in the Fall of 1995. According to this method, the air supply system for inflating the sleeves was triggered by an ECG machine to coincide with the patient's heart action, i.e., a cyclical pressure was applied to the legs as well as the abdomen of a patient via pressurized sleeves at the heart rate frequency. Such a system would be of little value to a patient in shock where the heart rate is very fast or perhaps non-existent. Heart failure of the myocardial infraction type, i.e., cessation of blood flow to an area of the heart, invariably results in an increase in the patient's pulse rate and a decrease in the patient's systolic pressure. Alternately applying and relieving pressure to a patient's legs and/or abdomen at elevated cyclical rates appears to have little effect on the movement of blood from one part of the body to another. We have found that the inertia forces involved, i.e., the masses of blood to be moved and the degree of elasticity of the blood vessels, are not conducive to sufficient increases in the flow of blood for pronounced pulmonary or cardiac activity rehabilitation at high cyclical rates, e.g., 70+ cycles/min.

Anti-shock or anti-gravity suits have been used for many years to apply forces, pneumatically or mechanically, to redistribute the blood in bodies of pilots and cosmonauts to support life or prevent black outs. Such suits, however, operate to apply pressure as needed and not typically on a cyclic regime.

Pneumatic Antishock Garments ("PASG") and Medical Antishock Trousers ("MAST") which encompass a patient's legs and lower abdomen have also been used to apply continuous (or substantially continuous) pressure to a patient's legs and lower abdomen to improve blood pressure in shock victims, curtail bleeding from wounds in the lower extremities and to immobilize the lower extremities for transport.

We have discovered that the application of a cyclical pressure on a patient's stomach and preferably also his or her legs, at a frequency not keyed to heart rate and preferably at a frequency lower than the normal heart frequency, provides improved results in cardiac resuscitation as well as pulmonary rehabilitation.

SUMMARY OF THE INVENTION

In accordance with the present method (and apparatus) of rehabilitating a patient's cardiac/pulmonary activity, inflatable/deflatable leg and abdominal cuffs are secured over the patient's leg(s) and abdominal areas, respectively. The leg and abdominal cuffs, when inflated, are arranged to apply pressure to the underlying vessels to force blood into the chest cavity and when deflated to accommodate the return of blood to the legs and abdomen. The cuffs are preferably inflated/deflated at a lower frequency than the normal heart rate frequency of 60–70 cycles/min. and most preferably within the range of 10 to 40 cycles/min. While the cyclical rate of inflation/deflation of the leg cuffs may be the same as for the abdominal cuff we have found that the leg cuffs may be inflated/deflated at a frequency lower than the frequency for the abdominal cuff, e.g., within the range of 0 to 40 cycles/min. It should be noted that good results have been obtained where the leg cuffs were inflated on a substantially continuous basis with deflation occurring once every 10 or so minutes to prevent injury or damage to tissue affected by the cessation of blood flow during the inflation mode of the cuff.

Additionally, an inflatable/deflatable chest cuff may be used in conjunction with the abdominal cuff alone or with both the leg and abdominal cuffs. The chest cuff functions in an out-of-phase relationship with the abdominal cuff to depress and force air out of the patient's lungs when the abdominal cuff is deflated and to allow breathable gas to enter the patient's lungs when the abdominal cuff is inflated.

Breathable gas such as oxygen or oxygen enriched air may be supplied to the patient from a conventional ventilator/resuscitator unit via a face mask, having inhalation and exhalation valves, during the operation of the cuffs. The breathable gas is periodically supplied to the face mask in synchronism with the inflation mode of the abdominal cuff, i.e., out-of-phase with the operation of the chest cuff.

The present invention, both as to it's organization and features, may best be understood by reference to the following description taken in conjunction with the appended drawings.

BRIEF DESCRIPTION OF THE DRAWINGS

FIG. 3 is a perspective view of an inhalation/exhalation valve for use in the facial mask of FIG. 1;

FIG. 4 is a cross-sectional view of the valve of FIG. 3; and

FIG. 5 is a perspective view of a MAST suit which may be used in the apparatus of FIG. 1 in lieu of the cuffs for the legs and abdomen.

DESCRIPTION OF THE PREFERRED EMBODIMENT

Figure 1:
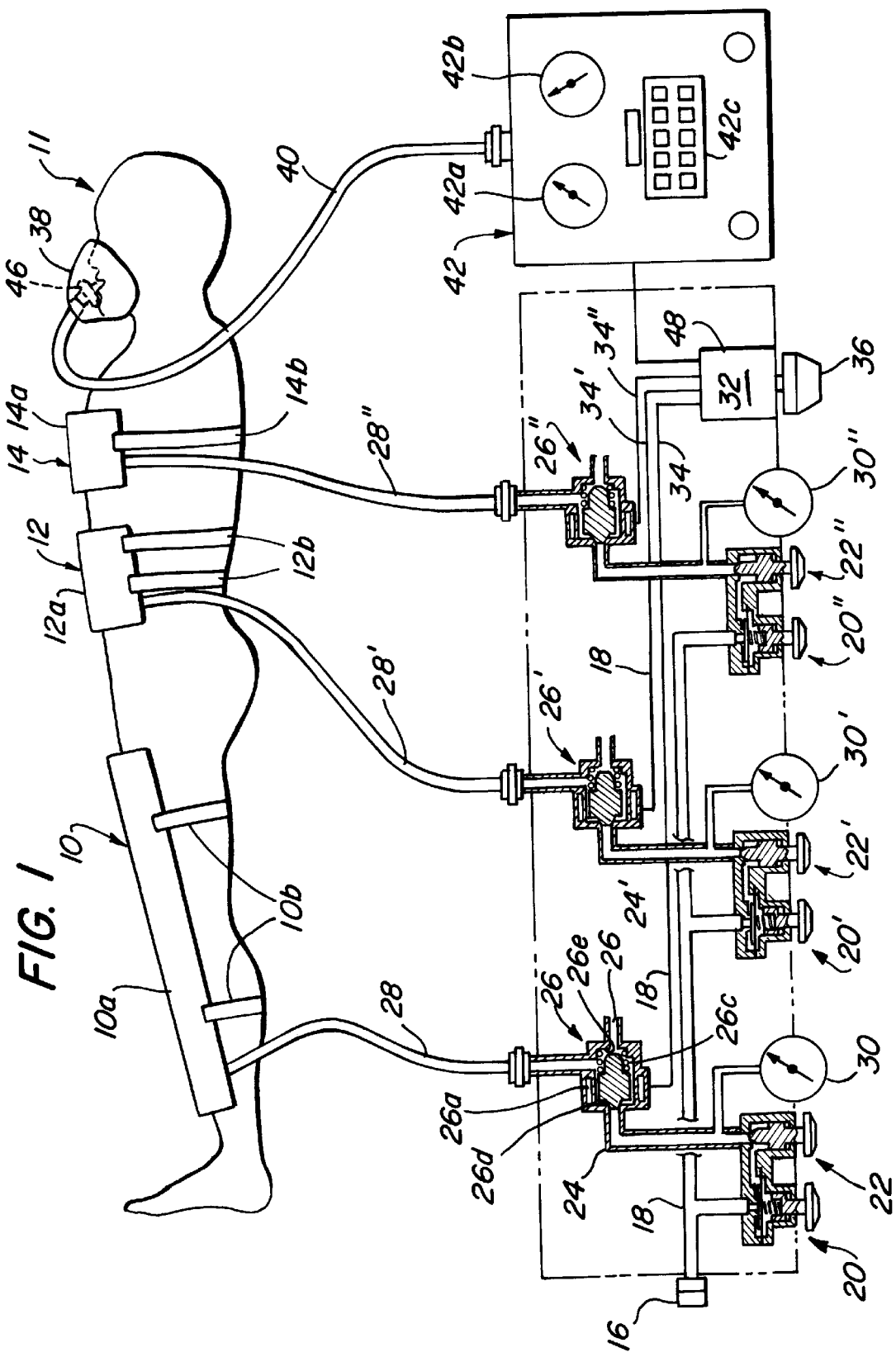
FIG. 1 is a schematic diagram of an apparatus in accordance with the present invention showing, in cross-section, the several valves for connecting the inflatable cuffs to a pressurized gas source.

Referring now to the drawings and particularly to FIG. 1, an inflatable leg bladder or cuff 10 is fitted over one or both legs of a patient 11 requiring rehabilitation or resuscitation of his or her cardiac/pulmonary system.

Each leg cuff comprises a pneumatically inflatable section 10a adapted to be secured over a patient's legs via straps 10b so that when the section 10a is inflated pressure is applied to the underlying vessels to force blood into the upper portion of the patient's body. An abdominal cuff 12, similar in construction to the leg cuff 10, includes an inflatable section 12a adapted to be secured over the patient's abdomen via straps 12b. The abdominal cuff in conjunction with the leg cuff(s) serves to force blood from the legs and abdomen into the chest cavity as will be explained in more detail. It should be noted that the cuffs may be in the form of inflatable sleeves which encompass the patient's legs or abdomen.

An optional chest cuff 14 includes an inflatable section 14a which is adapted to be secured over the patient's chest area via strap 14b. Gas, such as air, under pressure is supplied to each of the cuffs 10, 12 and 14 from a pressurized gas source 16 via a plurality of valves to be described. The source 16 may, for example, be in the form of an air compressor or a pressurized container of air or other gas.

Gas from the source 16 is supplied to the leg cuff(s) 10 via a line, hose or conduit 18, a manually adjustable pressure regulator 20, a manually controlled flow control valve 22, a line 24, a solenoid operated valve 26 and a line 28. A pressure gauge 30 provides an analog readout of the pressure in the line 24 (and the line 18 when the valve 22 is open). The solenoid valve 26 includes a coil 26, a moveable magnetically responsive valve core 26b and a spring 26c. The spring 26c biases the core 26d into engagement with a valve seat 26d to disconnect the cuff 10 and line 28 from line 24 when the coil 26a is deenergized. In this position, the line 28 is connected to a low pressure region, i.e., the atmosphere, via vent port 26d. When the coil 26a is energized the core 26b engages a seat 26e in the vent port and disconnects the line 28 from atmosphere. At the same time the valve 26 connects the lines 24 and 28. It should be noted that a pressure sensitive relief valve may be placed in vent port 26e, if desired, to provide a minimum back pressure, e.g., 2" to 3" of $H_2O$, to the gas escaping from the cuff 10 during the deflation mode.

The valves and lines for controlling the inflation/deflation of the abdominal and chest cuffs 12 and 14 are identical to those just described for the leg cuffs and are given the same reference numerals primed and double primed as shown. A control module 32 supplies current pulses to the solenoid coils 26a, 26a', and 26a", via conductors 34, 34' and 34" to alternately cause the several cuffs to inflate and deflate as will be explained in more detail in conjunction with FIG. 2. A manual control knob 36 may be provided to allow an operator to adjust the frequency of the current pulses applied to the solenoid coils.

An artificial lung ventilation system which may be used to ventilate the patient's lungs with oxygen or oxygen enriched air in conjunction with the movement of the blood from the patient's lower extremities includes a face mask 38, a line 40 and a conventional ventilator/respirator 42. The face mask 38 is provided with an inhalation/exhalation valve 46, shown, more particularly, in FIGS. 3 and 4. The valve 46 includes a cylindrical mouthpiece 46a which is adapted to be inserted into the patient's mouth and a cylindrical inlet section 46b with an enlarged flange 46c which snaps into a cooperating flange 46d on the mouthpiece.

A flexible diaphragm 46e with a central aperatured duck bill portion 46f allows gas from the ventilator 42 to enter the patient's airway during the inhalation mode as is illustrated by the arrows. During the inhalation mode the diaphragm 46 engages seat 46g to prevent the inlet gas from escaping to atmosphere. During the exhalation mode the pressure differential across the diaphragm causes the opening in the duck bill portion to close and also causes the diaphragm 46e to move away from the mouthpiece section, i.e., moves to the left in FIG. 4, thereby venting the interior of the mouthpiece section to atmosphere via vent ports 46h.

The ventilator/respirator 42 may include meters 42a and 42b for providing a visual display of the pressure and flow rate of the gas being supplied to the face mask 38. Manually operable control buttons 42c allow an operator to adjust such parameters. The ventilator 42 is operated in an out-of-phase relationship with the chest cuff so that when the chest cuff is inflated the ventilator is in the exhalation mode, i.e., no breathable gas being furnished to the patient and visa versa as will be explained in more detail. A conductor 48 connects the control module to the ventilator/respirator 42 for synchronizing the operation of the unit 42 and the valve 26".

Figure 2:
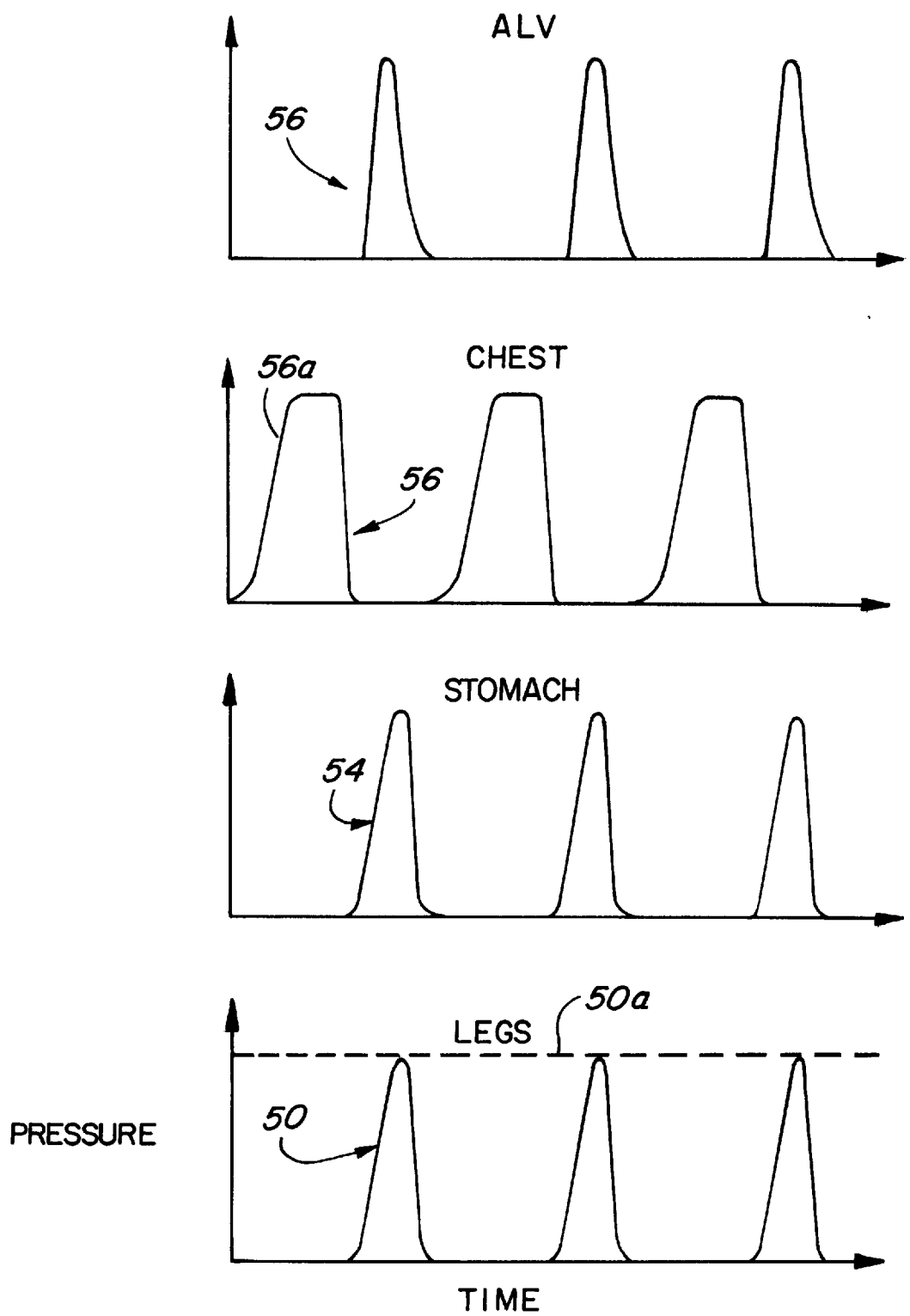
FIG. 2 is a group of waveform diagrams in which the pressure of the gas supplied to the several inflatable cuffs and the facial mask of the apparatus of FIG. 1 is plotted as a function of time.

Referring now to FIG. 2, the waveforms of the pressure of the gas applied to the leg, abdominal, and chest cuffs and to the face mask, are designated by the reference numerals 50, 52, 54 and 56, respectively. The maximum gas pressure applied to the leg cuffs is preferably within the range of about 0.08 to 0.20 $Kg/cm^2$ (and most preferably about 0.1 $Kg/cm^2$) while the maximum pressure applied to the abdominal cuff is preferably within the range of about 0.1 to 0.3 $Kg/cm^2$ (and most preferably about 0.25 $Kg/cm^2$). The maximum pressure in the chest cuff is preferably within the range of about 0.1 to 0.25 $Kg/cm^2$ and most preferably about 0.2 $Kg/cm^2$. The maximum pressure in the face mask at the end of the inhalation phase is preferably about 20 cm of $H_2O$ (water column) and 5 cm of $H_2O$ at the end of the exhalation phase.

The cyclical rate of the pressure pulses to the leg and abdominal cuffs is preferably within the range of about 10–40 cycles/min. and most preferably within the range of about 20 to 25 cycles/min., as set by the controller 32. A rate of about 20 cycles/min. appears to provide very good results with adult patients.

The objective of the leg and abdominal cuffs is to enhance the circulation of blood in cases of failed or faltering heart action or simply for therapeutic purposes. The cuffs provide external compression of large body masses in a pulsating manner such that blood is caused to flow by virtue of the resulting pumping action.

Cyclical rates and pressures can be selected to maximize the amount of blood circulated. The most efficient rate is determined by the time required for inflow of blood to the tissues when the pressure is relaxed. If the time interval is too short due to a high cyclical rate, incomplete filling will occur and thus the amount of blood moved one each compression cycle will be diminished. If, on the other hand, the cyclical rate is slower than that which will allow nearly complete filling, the total blood moved will also be reduced.

The optimum values of such parameters appear to vary with the size and to some extent with the condition of the patient and therefore trained specialists may adjust the parameter values to optimize the results.

The use of an inflatable/deflatable chest cuff in conjunction with a ventilator/respirator and face mask for restoring or supplementing a patient's breathing function is described in U.S. Pat. No. 5,492,115 ("'115 patent") which issued to Vladimir V. Abramov (a named co-inventor of the present application) and Juriy V. Novikov, on Feb. 6, 1996. In certain cases of cardiac malfunction there is a need to use the chest cuff 14 and/or ventilator/respirator in addition to one or both of the lower extremity cuffs (leg, abdominal cuffs). As is noted in FIG. 2, the pulsating pressure waves applied to the chest cuff are out-of-phase with the pressure waves applied to the abdominal cuff. The pressure wave 56 applied to the chest cuff preferably lasts for about 40–45% of the time for one cycle, e.g., a duty cycle of about 40% to 45%. The leading edge 56a of the chest cuff pressure wave is determined by the rate at which gas flows into the cuff as set, for example, by the valve 22". The maximum pressure in the chest cuff is set by the pressure regulator 20".

Breathable air is supplied to the face mask 38 in an out-of-phase relationship with the inflation mode of the chest cuff as is explained in detail in the '115 patent and as is shown in FIG. 2.

The following patients were treated with the cardiac resuscitator of this invention, incorporating only the leg and abdominal cuffs or all three cuffs during August of 1996 in Russia:

CASE 1

A male, age 23, was hit by a car on the road. Diagnosis—closed fracture of thigh bone (left leg). Shock IV degree. After 15 minutes the patient was brought to the clinic. The patient's arterial pressure was 60/40 millimeters of mercury column and this pulse rate was 200 beats per minute.

400 ml of polyglucine with hydrocortisone was transfused into the patient with no noticeable beneficial effect. The cardiac resuscitator of the invention was used in the "legs-abdomen" mode. After 40 seconds blood pressure reached 100/60 mm of mercury column and within the next 15 seconds the pressure reached 115/65 mm of mercury column. The pulse rate was 95. The abdomen bladder was then turned off. The pressure to the leg bladders was reduced slowly over a fifteen minute period and then turned off. The patient's blood pressure and pulse rate remained about the same. The patient was in satisfactory condition.

CASE 2

A male, age 40, suffered a heat stroke (overheating). His pulse rate was 170 (beats per minute) "thread-typed", and his blood pressure was 65/30. The patient was unconscious. The doctors used a standard oxygen device for artificial lung ventilation along with an intravenous injection of 5% glucose and prednizolone, but it did not provide any noticeable beneficial effect. A cardiac resuscitator was used in the "legs-abdomen" mode. After 35 seconds the patient's pulse rate decreased to 100 beats per minute and his blood pressure rose to 110/80. Fifteen seconds later the patient became conscious. The device was turned off. The patient was in satisfactory condition.

CASE 3

A male, age 65, suffered a cardiac arrest at home. During the previous two years he had been under medical care due to frequent cardiac arrests. The patient was unconscious and his pulse, 15–20 beats per minute, was of the "threaded-type" and interrupted. His blood pressure was 40/0; his face and hands were pale with a bluish cast.

The cardiac resuscitator of the invention was used in the "legs-abdomen-chest" mode. After two minutes the patient's blood pressure rose to 90/55 and in 30 seconds the blood pressure stabilized at 100/60. The patient's pulse rate was 90. The chest cuff was then deactivated. The patient's face was rosy, but he was unconscious. After 5 minutes the entire unit was turned off. Ten minutes later the patient's blood pressure dropped to 60/40. Adrenaline was administered to the patient and his blood pressure increased to 80/50. The patient had strongly expressed bradiocardia. Twenty minutes after receiving the medication the patient's blood pressure began to drop again.

The cardiac resuscitator was again applied to the patient in the "legs-abdomen" mode only. After 30 seconds the patient's blood pressure increased to 105/60 and he became conscious with an even heartbeat and a pulse rate of 75/80 beats per minute. Then the cardiac resuscitator was then used for 4½ hours in the "legs-abdomen" mode with two 5 minute breaks for testing patient's condition. During this 4½ hour period, the patient's cardiac vascular parameters remained satisfactory; however, during the breaks the parameters drastically got worse. The decision was made to transport the patient to the Institute of Cardiac and Vascular Surgery for operation.

It should be noted that the valves for controlling the inflation/deflation of the cuffs in the Russian tests were of the diaphragm type as described in the '115 patent.

While it is believed to be preferable to inflate and deflate the leg cuffs at the same cyclical rate as the abdominal cuff, we have found that the leg cuffs can be operated at a lower frequency including zero cycles/min., as long as the cuffs are deflated periodically, e.g., once every 10 minutes or so, to prevent injury or damage to tissues affected by the cessation of blood flow during the time that the leg cuffs are inflated. Dashed line 50a in FIG. 2 illustrates a constant pressure being applied to the leg cuffs.

FIG. 5 illustrates a MAST suit which may be employed in lieu of separate cuffs for the patient's legs and abdomen. The MAST suit includes separate inflatable leg cuffs or sleeves 60 which are connected to an abdominal cuff or sleeve 62 by a zipper 64. Velcro straps 66 allow a doctor, paramedic or nurse to tightly wrap the several sections of the suit around the legs and lower torso of a patient so that when the sleeves are inflated appropriate pressure will be applied to the underlying vessels and veins. Hoses 68 and 70 allow fluid to enter and exit the leg and abdominal cuffs, respectively. Such hoses may be connected to the valves 26 and $26^1$ of the apparatus of FIG. 1.

There has thus been described a novel method and apparatus for rehabilitating a patient's cardiac and/or pulmonary activity. Various modifications and additions to such methods and apparatus will become apparent to those skilled in the art without involving any departure from the scope and spirit of our invention as defined in the appended claims.

What is claimed is:

1. A cardiac resuscitation apparatus for transferring masses of blood from a patient's leg and abdominal areas to an upper regions of a patient's body to increase arterial pressure independently of a patient's heart action comprising:

a source of pressurized gas;

a inflatable abdominal cuff adapted to extend over a patient's abdomen;

at least one inflatable leg cuff adapted to extend over at least an upper portion of one of a patient's legs;

valve means connected between the pressurized source, the cuffs and a region of low pressure for selectively connecting the cuffs to the pressurized gas source and to the low pressure region; and a valve control means coupled to valve means for controlling the valve means to periodically and alternately connect the cuffs to the pressurized gas source and to the region of low pressure independently of the patient's heart action whereby the inflation/deflation cycle of the abdominal cuff is less than about 40 cycles/min, the inflation/deflation cycle rate of the leg cuff being between zero in which the leg cuff is continuously inflated and the inflation/deflation cycle rate of the abdominal cuff.

2. The invention of claim 1 wherein said at least one inflatable leg cuff comprises a leg cuff adapted to extend over each of the patient's legs.

3. The invention of claim 2 further including a pressure regulator individually coupled to each of the abdominal and leg cuffs to regulate the maximum allowable pressure in each of the cuffs.

4. The invention of claim 3 wherein the pressure regulators are set so that the maximum pressure in the abdominal cuff is within the range of about 0.20 to 0.30 kg/cm$^2$ and the maximum pressure is the leg cuffs is within the range of about 0.10 to 0.25 kg/cm$^2$.

5. The invention of claim 3 including a flow regulator individually coupled to each of the abdominal and leg cuffs to regulate the maximum gas flow rate into the cuffs.

6. The invention of claim 1 wherein the valve control means is arranged to provide the same inflation/deflation cycles for the leg and abdominal cuffs.

7. The invention of claim 1 further including the following apparatus to additionally provide cardiac resuscitation:

an inflatable chest cuff adapted to extend over a patient's chest, the valve means including a valve connected between the pressurized source and the chest cuff to periodically inflate and deflate the chest cuff in an out of phase relationship with respect to the inflation/deflation cycle of the abdominal cuff.

8. The invention of claim 7 further including:

a face mask for providing fluid communication to the patient's lungs;

a source of breathable gas;

a ventilation valve connected between the face mask and the breathable gas source; and a ventilation valve controller means for controlling the ventilation valve to periodically connect the face mask and the patient's lungs to the breathable gas source in synchronism with the inflation/deflation cycle of the chest cuff so that the breathable gas is supplied to the patient during the deflation mode of the chest cuff.

9. The invention of claim 8 further including a pressure regulator coupled to the chest cuff to regulate the maximum allowable pressure in the chest cuff.

10. The invention of claim 9 wherein the chest cuff pressure regulator is arranged to set the maximum allowable pressure in the chest cuff at about 0.2 kg/cm$^2$.

11. The invention of claim 10 further including a flow regulator coupled to the chest cuff to regulate the maximum gas flow rate into the chest cuff.

12. A cardiac/pulmonary resuscitator comprising:

a face mask for providing fluid communication to a patient's lungs;

a ventilator including a source of pressurized gas, at least a portion of said gas being breathable; the ventilator being connected to the face mask for periodically connecting the face mask to the gas source for transferring breathable gas to the mask;

an inflatable chest cuff adapted to extend over a patient's chest;

a chest cuff valve connected between the pressurized gas, the chest cuff and a low pressure region, whereby the chest cuff is inflated to apply pressure to a patient's chest when connected to the pressurized gas source and is deflated to relieve pressure on a patient's chest when connected to the low pressure region;

a valve controller coupled to the chest cuff valve to operate the valve so that the chest cuff is periodically and alternately connected to the pressurized gas source and the low pressure region to provide an inflation/deflation cycle of the chest cuff within the range of about 10–40 cycles/min, the inflation/deflation cycle of the chest cuff being out-of-phase with the operation of the ventilation valve;

an inflatable abdominal cuff adapted to extend over a patient's abdomen;

an abdominal cuff valve connected between the pressurized gas source, the abdominal cuff, and the low pressure region;

at least an inflatable leg cuff adapted to extend over one of a patient legs;

a leg cuff valve connected between the pressurized gas source, the low-pressure region; and the valve controller being further coupled to the abdominal cuff valve and the leg cuff valve to operate the valves independently of a patient's heart action so that the abdominal and leg cuffs are periodically and alternately connected to the pressurized gas source and the low pressure region to provide an inflation/deflation cycle for the abdominal cuff which is out-of-phase with the chest cuff cycle and an inflation/deflation cycle for the leg cuff between zero, in which the leg cuff is continuously inflated and 40 cycles per minute.

13. The invention of claim 12 further including a pressure regulator individually coupled to each of the chest and abdominal cuffs for regulating the maximum allowable pressure in each of said cuffs.

14. The invention of claim 13 wherein the pressure regulators are set so that the maximum pressure in the chest and abdominal cuffs is within the ranges of about 0.15–0.30 kg/cm$^2$.

15. A method of enhancing a patient's cardiac activity comprising the steps of:

placing an inflatable cuff over the abdominal area and another inflatable cuff over at least the upper leg portion of the patient, each cuff being arranged to apply pressure to the underlying vessels when inflated to divert blood to the upper portions of the patient's body;

inflating and deflating the abdominal cuff at a frequency less than about 40 cycles/min. independently of the patient's heart action; and inflating and deflating the leg cuff at a frequency within the range of about 0 to less than 40 cycles/min with the leg cuff being continuously inflated at the zero cycle rate.

16. The method of claim 15 wherein the leg cuff is inflated on a substantially continuous basis.

17. The method of claim 16 wherein the frequency of the inflation/deflation rate of the abdominal cuff is within the range of about 15–25 cycles/min.

18. The method of claim 17 wherein the frequency of the inflation/deflation cycle of the abdominal cuff is about 20 cycles/min.

19. The method of claim 16 further comprising the step of maintaining the leg cuff in an inflated state except for sufficient intervals of deflation to prevent tissue injury.

20. The method of claim 15 wherein the frequency of the inflation/deflation rate of the leg cuff is the same as that for the abdominal cuff.

21. The method of claim 16 further including the step of placing an inflated cuff over the chest area of the patient and inflating/deflating the chest cuff in an out-of-phase relationship with the inflation/deflation of the abdominal cuff.

22. A method of rehabilitating a patient's cardiac/pulmonary activity comprising the steps of:

fitting the patient with a face mask which provides fluid communication to the patient's lungs;

providing a source of breathable gas under pressure;

placing one inflatable/deflatable chest cuff over the patient's chest area and another inflatable/deflatable cuff over the patient's abdominal area, the chest cuff, when inflated, being arranged to depress the chest and force air out of the patient's lungs, the abdominal cuff being arranged, when inflated to apply pressure to the underlying vessels to direct blood into the patient's chest area;

inflating and deflating the chest cuff and the abdominal cuff independently of the patient's heart action and in synchronism with each other but in an out-of-phase relationship at a frequency within the range of about 10 to 40 cycles/min.;

connecting the face mask to the breathable gas source to supply breathable gas to the face mask and the patient's lungs in synchronism with the inflation mode of the abdominal cuff;

placing an additional inflatable/deflatable cuff over at least the upper portion of each of the patient's legs and inflating and deflating the leg cuffs at a frequency of about 0 to 40 cycles/min, with the leg cuffs being continuously inflated at the zero cycle rate.

23. The method of claim 22 wherein the inflation/deflation frequency of the abdominal cuff is within the range of about 15 to 25 cycles/min.

24. The method of claim 23 wherein the inflation/deflation frequency of the abdominal cuff is about 20 cycles/min.

* * * * *